United States Patent [19]

Gabriel et al.

[11] 4,256,875
[45] Mar. 17, 1981

[54] EXTRACTION OF SENNOSIDES

[75] Inventors: Jean P. Gabriel, St. Symphorien; Marcel Dumont, St. Cyr-sur-Loire; Robert Guillé, Tours, all of France

[73] Assignee: Synthelabo, Paris, France

[21] Appl. No.: 29,007

[22] Filed: Apr. 11, 1979

[30] Foreign Application Priority Data

Apr. 14, 1979 [FR] France .............................. 78 11023

[51] Int. Cl.$^3$ ............................................ C07H 15/24
[52] U.S. Cl. ........................................ 536/4; 424/180
[58] Field of Search ............................................ 536/4

[56] References Cited

U.S. PATENT DOCUMENTS

| | | | |
|---|---|---|---|
| 3,089,814 | 5/1963 | Blaich et al. | 536/4 |
| 3,364,113 | 1/1968 | Friedmann et al. | 536/4 |
| 3,517,269 | 6/1970 | Menssen et al. | 536/4 |

FOREIGN PATENT DOCUMENTS

| | | |
|---|---|---|
| 2315301 | 1/1977 | France . |
| 744876 | 2/1956 | United Kingdom . |

*Primary Examiner*—Johnnie R. Brown
*Assistant Examiner*—Blondel Hazel
*Attorney, Agent, or Firm*—Wegner & Bretschneider

[57] ABSTRACT

A process for the extraction of sennosides from senna folioles and follicles, comprising the rapid exhaustion of the plant by means of cold water, in a neutral or slightly alkaline medium, followed by acidification and extraction with butanol.

This process minimizes oxidation and hydrolysis of the product and achieves improved yields and purity.

5 Claims, No Drawings

EXTRACTION OF SENNOSIDES

DESCRIPTION

The present invention relates to a process for the extraction of sennosides from senna folioles and follicles.

Sennosides, which are pharmacologically valuable products from the various CASSIA, are dianthrone glucosides and are particularly sensitive to oxidation and hydrolysis. The extraction of sennosides has hitherto been carried out either in a boiling aqueous medium, or in an alcoholic medium, namely a methanolic or ethanolic medium, and the problem in industrial extraction is to obtain adequate yield and purity.

The present invention provides a process for the extraction of sennosides from senna folioles and follicles, comprising the rapid exhaustion of the plant by means of cold water, in a neutral or slightly alkaline medium, followed by acidification and extraction with butanol.

Sennosides are insoluble or very sparingly soluble in non-polar solvents and they are virtually insoluble in ethanol and methanol. Their solubility is optimum in a water-miscible organic solvent having a water content of 30%, but even then, their rate of dissolution remains very slow. It has, however, been found that, although pure sennosides are relatively insoluble in water when they are in the native state in the plant, they very readily pass into an aqueous phase, this passage being further improved in a medium containing a small amount of bicarbonate, from which aqueous phase they can be recovered by the extraction with butanol.

The present process thus minimizes hydrolysis and oxidation by providing an extraction solvent which exhausts the plant in a short time at a pH which is not far from neutral and avoids heat as far as possible. Concentration of the butanol phase in vacuo, at a temperature which does not exceed 50° C., causes the sennosides to crystallise with a purity of more than 60%.

The extraction of the sennosides into an aqueous medium is facilitated when the folioles have been washed beforehand with a solvent such as ethanol, methylene chloride, hexane or benzene to remove resins, waxes and chlorophylls. In addition, before the butanol extraction of the aqueous phase, which contains a large amount of sennosides, it is advantageous to treat it with ethyl acetate, thereby removing flavones and free anthraquinone derivatives. These two improvements make it possible to obtain sennosides of more than 70/80% purity.

The following Examples illustrate the invention.

EXAMPLE 1

100 g of senna are exhausted with 1 liter of ordinary water.

The aqueous solution is acidified, with HCl, to pH 2.5 and extracted with 400 ml of ethyl acetate. The aqueous phase is then extracted 3 times with 1,100 ml of butanol.

This butanol phase is concentrated to 50 ml at 50° C. in vacuo and then left to stand for 1 night. The precipitate is then isolated on a Büchner funnel and 2.3 g of extract, containing 72.2% of pure sennosides, and thus obtained.

EXAMPLE 2

100 g of senna are first exhausted with absolute ethanol.

The dried plant is bruised and extracted with 10 times its weight of water to which 0.25% of sodium bicarbonate has been added.

The aqueous phase is acidified with 60 ml of acetic acid (pH 3.5) and extracted with 2 liters of butanol.

The butanol phase is concentrated to 50 ml in vacuo at 50° and then left to stand in a refrigerator (4°) for 1 hour 30 minutes.

The precipitate is then isolated and dried. This yields 2.800 g of 82% pure extract.

EXAMPLE 3

200 g of untreated senna are exhausted with water containing 0.25% of sodium bicarbonate.

The aqueous phase is acidified to pH 1 with the aid of concentrated HCl and is then extracted with 3 liters of butanol.

The butanol phase is then concentrated to 150 ml at 70° C. in vacuo and is subsequently left to stand for 2 hours.

The crystalline product is isolated and dried. This yields 4.300 g of 64% pure product.

EXAMPLE 4

100 g of senna are washed with 700 ml of hexane and dried.

The plant is exhausted with 10 times its weight of water.

The aqueous phase is acidified to pH 2.5 with concentrated HCl and extracted with 1.100 liters of butanol.

The butanol phase is then concentrated to 100 ml in vacuo at 50° and left to stand for 1 night.

The product is isolated on a Büchner funnel and dried. This yields 2.03 g of 68.5% pure product.

EXAMPLE 5

Method for the Industrial Extraction of High-grade Sennosides

Raw Materials
Unwashed and unground senna folioles: 100 kg
Ordinary water: 1,050 liters
Butanol: 600 liters
Pure hydrochloric acid: 6 liters
Technique The senna and 650 liters of water are charged into a percolator with a filter base. The solvent is circulated in a closed circuit for 3 hours by means of a pump. The resulting solution is drawn off. The percolator is recharged with 300 liters of water and this water is recycled for a further 2 hours 30 minutes.

The plant is rinsed with 100 liters of water. This yields 900 liters of liquor.

In a mixing bath, these liquors are acidified to pH 2.5 with about 6 liters of concentrated HCl.

This acid phase is then extracted immediately with 600 liters of butanol in a liquid/liquid extractor.

In a continuous concentrator, the butanol phase is concentrated at 40° C. in vacuo until 50 liters of concentrate are obtained. This is left to stand for 48 hours. The crystalline precipitate is isolated by filtration on a Büchner funnel and then dried in a vacuum cabinet.

This yields about 2 to 2.5 kg of product containing a minimum of 60% of acid sennosides.

The process of the invention makes it possible to obtain sennosides of high grade and with a very good yield.

We claim:

1. A process for the extraction of sennosides from senna folioles or follicles, comprising rapidly exhausting said senna folioles or follicles with cold water in a neutral or slightly alkaline medium, followed by acidification and extraction of the thus exhausted product with butanol.

2. A process according to claim 1, wherein the water is rendered slightly alkaline with sodium bicarbonate.

3. A process according to claim 1 or 2, wherein the acidification is carried out by means of hydrochloric acid.

4. A process according to claim 1 or 2, wherein said senna folioles or follicles are washed with a solvent selected from ethanol, methylene chloride, hexane and benzene prior to exhausting.

5. A process according to claim 1 or 2, wherein said exhausted product which contains a large amount of sennosides is treated with ethyl acetate prior to said acidification.

* * * * *